(12) United States Patent
Osypka et al.

(10) Patent No.: US 9,061,120 B2
(45) Date of Patent: Jun. 23, 2015

(54) CATHETER CONTROL MECHANISM AND STEERABLE CATHETER

(75) Inventors: Thomas P. Osypka, Palm Harbor, FL (US); Timothy L. Sass, Port Richey, FL (US); Erik W. Delly, St. Petersburg, FL (US); Jeff Jeffrey Drum, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 1155 days.

(21) Appl. No.: 12/603,584

(22) Filed: Oct. 21, 2009

(65) Prior Publication Data

US 2010/0106141 A1    Apr. 29, 2010

Related U.S. Application Data

(60) Provisional application No. 61/107,227, filed on Oct. 21, 2008, provisional application No. 61/178,409, filed on May 14, 2009.

(51) Int. Cl.
| | | |
|---|---|---|
| *A61M 25/00* | (2006.01) | |
| *A61M 5/178* | (2006.01) | |
| *A61M 37/00* | (2006.01) | |
| *A61M 25/01* | (2006.01) | |
| *A61B 5/042* | (2006.01) | |

(52) U.S. Cl.
CPC .......... *A61M 25/0147* (2013.01); *A61B 5/0422* (2013.01); *A61M 25/0136* (2013.01); *A61M 25/0141* (2013.01)

(58) Field of Classification Search
CPC ...................... A61M 25/0147; A61M 25/0136; A61M 25/0141; A61B 5/0422
USPC .......... 604/95.04–95.05, 164.13, 165.04, 528
See application file for complete search history.

(56) References Cited

U.S. PATENT DOCUMENTS

| | | | | |
|---|---|---|---|---|
| 3,605,725 | A | * | 9/1971 | Bentov ........................... 600/434 |
| 4,456,017 | A | * | 6/1984 | Miles ............................. 600/585 |
| 5,037,391 | A | * | 8/1991 | Hammerslag et al. ........ 604/528 |
| 5,676,653 | A | * | 10/1997 | Taylor et al. ............... 604/95.04 |
| 6,978,185 | B2 | | 12/2005 | Osypka |
| 7,158,837 | B2 | | 1/2007 | Osypka et al. |
| 2005/0060013 | A1 | | 3/2005 | van den Nieuwenhof et al. |
| 2006/0095107 | A1 | | 5/2006 | Osypka |

OTHER PUBLICATIONS

Nzayinambaho, K., et al., "Radiofrequency Ablation for Supraventricular Tachyarrhythmias," Cardiovascular Center, O.L.V. Hospital, Aalst, Belgium, vol. 3, No. 2, 1993.

* cited by examiner

*Primary Examiner* — Bhisma Mehta
*Assistant Examiner* — Bradley G Thomas, Jr.
(74) *Attorney, Agent, or Firm* — Locke Lord LLP; Scott D. Wofsy; Christopher J. Capelli

(57) ABSTRACT

A steerable multi-polar lead shaft assembly includes a core member extending longitudinally through the shaft assembly, a plurality electrically conductive elements disposed within the core member, a plurality of steering wires circumferentially distributed about the core member. A control mechanism for a steerable catheter, such as the steerable multi-polar lead assembly, includes a mounting portion adapted to engage a steerable shaft, a stem extending from the mounting portion, a swivel joint arranged at a proximal end of the stem, a control yoke rotatably mounted on the swivel joint, adapted to engage a plurality of steering wires of the steerable catheter, and a handle connected with the yoke, adapted for direct manipulation by a user.

7 Claims, 13 Drawing Sheets

CATHETER CONTROL MECHANISM AND STEERABLE CATHETER

CROSS-REFERENCE TO RELATED APPLICATIONS

This application claims the benefit of priority to U.S. Provisional Patent Application No. 61/178,409 filed May 14, 2009 and to U.S. Provisional Patent Application No. 61/107,227 filed Oct. 21, 2008. This application is also related to U.S. patent application Ser. No. 11/261,304, filed Oct. 28, 2005, published as U.S. Patent Application Publication Number 2006/0095107. Each of the aforementioned applications is incorporated herein by reference in its entirety. U.S. patent application Ser. No. 10/911,975, filed Aug. 5, 2004, published as U.S. Patent Application Publication Number 2005/0060013, and U.S. Pat. Nos. 6,978,185 and 7,158,837 are each also incorporated herein by reference in its entirety.

FIELD OF THE INVENTION

The present invention relates to surgical catheters and leads. Particularly, the present invention is directed to control mechanisms for surgical catheters and leads for use in cardiac procedures, such as cardiac pacing, mapping and ablation, for use in diagnosing and treating conditions such as cardiac arrhythmias, which are characterized by abnormal electrical impulses in the heart, and which include fibrillations, tachycardias and the like. Devices in accordance with the present invention are adaptable to many different applications, and in accordance with a preferred aspect of the invention are adapted for use in cardiac radio-frequency ablation procedures.

DESCRIPTION OF RELATED ART

A variety of medical catheter and lead devices are known in the art for performing medical procedures, including cardiac procedures, such as access catheters, pacing leads, diagnostic probes and electrosurgical tools.

Currently, electrophysiology catheters ("EP catheters") for use in cardiac ablation procedures are only capable of uni-directional or bi-directional bending. There remains a need in the art for a steerable catheter and/or lead structure that more agile in manipulation, durable, inexpensive, and easy to manufacture. There also remains a need in the art for control mechanisms capable of reliably and intuitively controlling such catheters. The present invention provides a solution for these needs.

SUMMARY

The purpose and advantages of devices constructed in accordance with the invention are set forth in and are apparent from the description that follows. Additional advantages of the invention will be realized and attained through the related methods and systems hereof, particularly pointed out in the written description and claims hereof, as well as from the appended drawings.

The invention includes, in one aspect, a steerable multi-polar lead shaft assembly including a core member extending longitudinally through the shaft assembly, a plurality of concentric helical electrically conductive elements, disposed within the core member, a plurality of steering wires circumferentially distributed about the core member, a rigid steering ring provided in a distal end portion of the shaft assembly operatively connected to the plurality of steering wires, and a plurality of electrodes provided in the distal end portion of the shaft assembly, each in electrical communication with at least one of the electrically conductive elements.

In another aspect, the invention includes a control mechanism for a steerable catheter including a mounting portion adapted to engage at least a steerable shaft to be controlled by the control mechanism, a stem extending from a mounting portion, a swivel joint arranged at a proximal end of the stem, a control yoke rotatably mounted on the swivel joint, adapted to engage a plurality of steering wires of the steerable catheter, and a handle connected with the yoke adapted for direct manipulation by a user.

The swivel joint can be configured, such that the yoke is provided on an axially rear portion thereof (See e.g., FIGS. 1-6). Alternatively, the swivel joint can be configured, such that the yoke is provided on a radially upper portion thereof (See e.g., FIGS. 7-25).

The swivel joint and the control yoke can be configured for mutually exclusive orthogonal movement, the handle being restrained at any one time to either forward-backward movement or left-right movement. A plurality of parallel grooves can be provided in one of the swivel joint and the control yoke for mating respectively with a corresponding plurality of protrusions on the other of the swivel joint and the control yoke. The corresponding protrusions can be colinear with a corresponding first groove to permit movement of the handle along a first direction. The protrusions can correspond respectively with at least second and third grooves to permit movement of the handle along a second direction.

It is to be understood that both the foregoing general description and the following detailed description are exemplary and are intended to provide explanation of the invention.

BRIEF DESCRIPTION

The accompanying drawings, which are incorporated in and constitute part of this specification, are included to illustrate and provide a further understanding of the devices, and related methods of the invention. Together with the description, the drawings serve to explain the principles of the invention, wherein.

DETAILED DESCRIPTION

Reference will now be made in detail to selected preferred embodiments of the invention, examples of which are illustrated in the accompanying drawings.

Figures 1, 2:
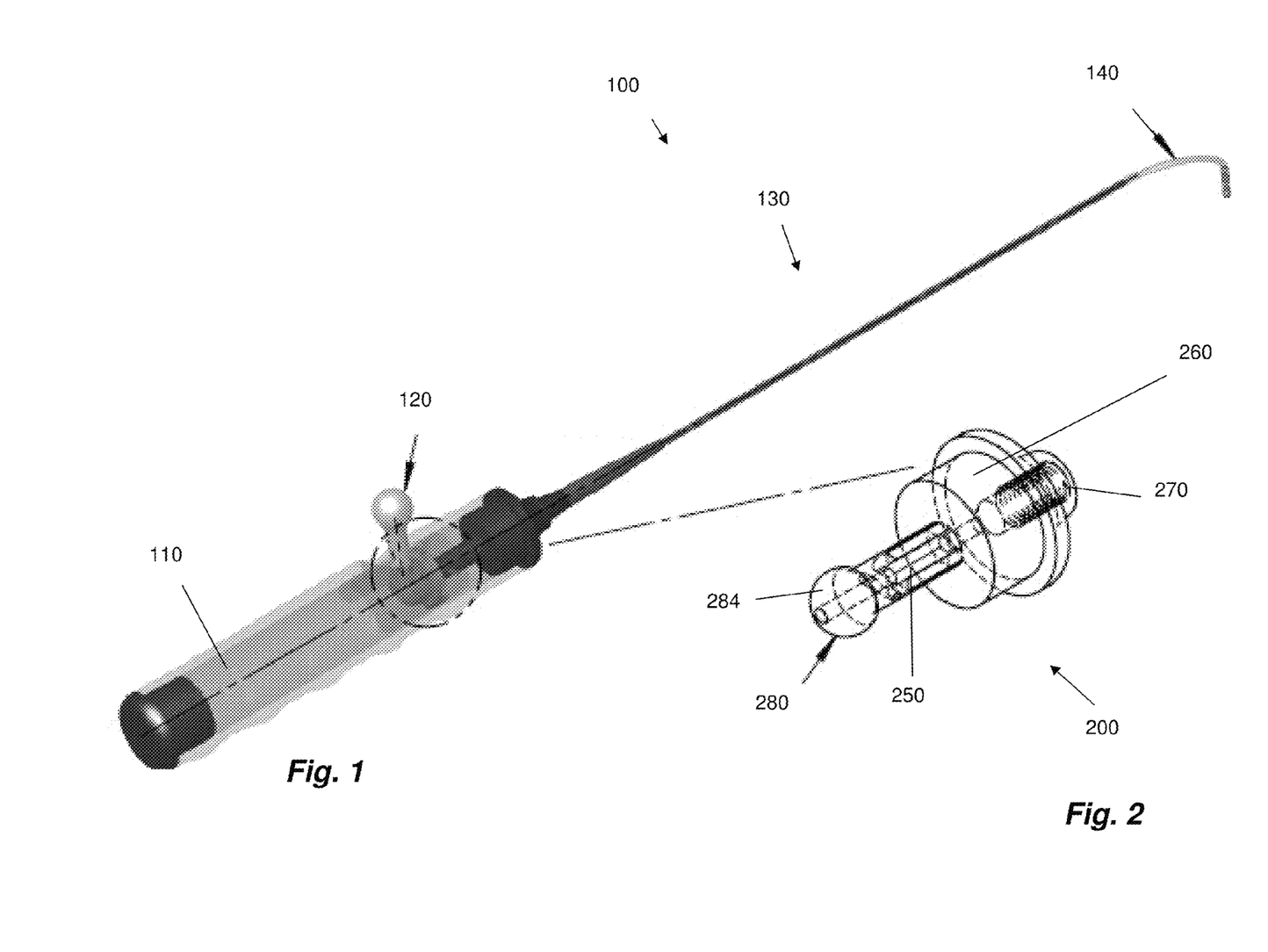
FIG. 1 is an isometric view of a first representative embodiment of a steerable catheter shaft assembly and catheter control mechanism in accordance with the present invention, wherein a handle thereof is turned toward the right, resulting in the distal end portion of the catheter being turned to the right.
FIG. 2 is an isometric wire frame view of an example control body portion of a control mechanism for a steerable catheter shaft assembly in accordance with the invention.

In accordance with the invention, for the purpose of illustration and not limitation, a steerable catheter lead assembly is shown in FIG. 1, and designated by reference number 100.

Figure 6:
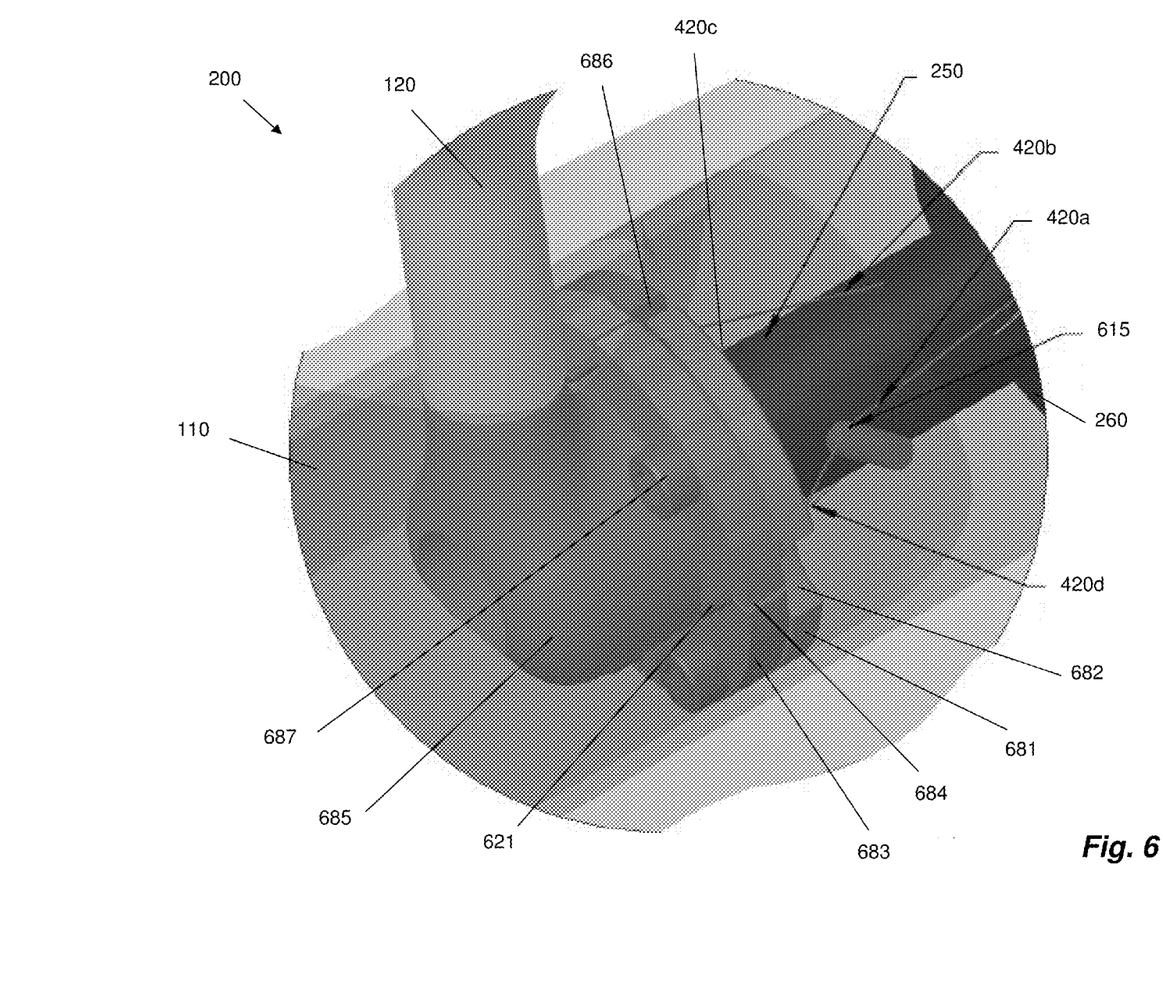
FIG. 6 is an isometric detail view of a control mechanism of a steerable catheter in accordance with the invention, including the body portion thereof illustrated in FIG. 2.

The steerable lead assembly includes a main handle 110, main shaft 130, steerable distal shaft portion 140 and a control handle 120 operatively connected with a control assembly 200, as best seen in FIGS. 2 and 6, for example.

Referring to FIGS. 2 and 6, a control assembly 200, provided in the main handle 110 of the catheter lead assembly 100 includes at its proximal end, a swivel joint 280, embodied as a spherical ball joint. The swivel joint 280 allows for multi-axis movement of the control handle 120, which in-turn manipulates steering wires 420a, 420b, 420c, 420d (See FIGS. 4-6). The swivel joint 280 is set off from a control body 260 by a stem 250. The control body 260 includes a distal engagement portion 270 for connecting to the shaft 130, and also facilitates assembly with the main handle 110, by engaging an inner wall of the main handle 110, when assembled. The stem 250, as best seen in FIG. 6, for example, supports guide pins 615, among other features, which facilitate manipulation of the steering wires 420a, 420b, 420c, 420d, the operation of which will be discussed in more detail below.

The control body 260 also includes, at its distal end, respective passages for guiding the steering wires 420 therethrough and into the shaft 130.

Figures 3, 4:
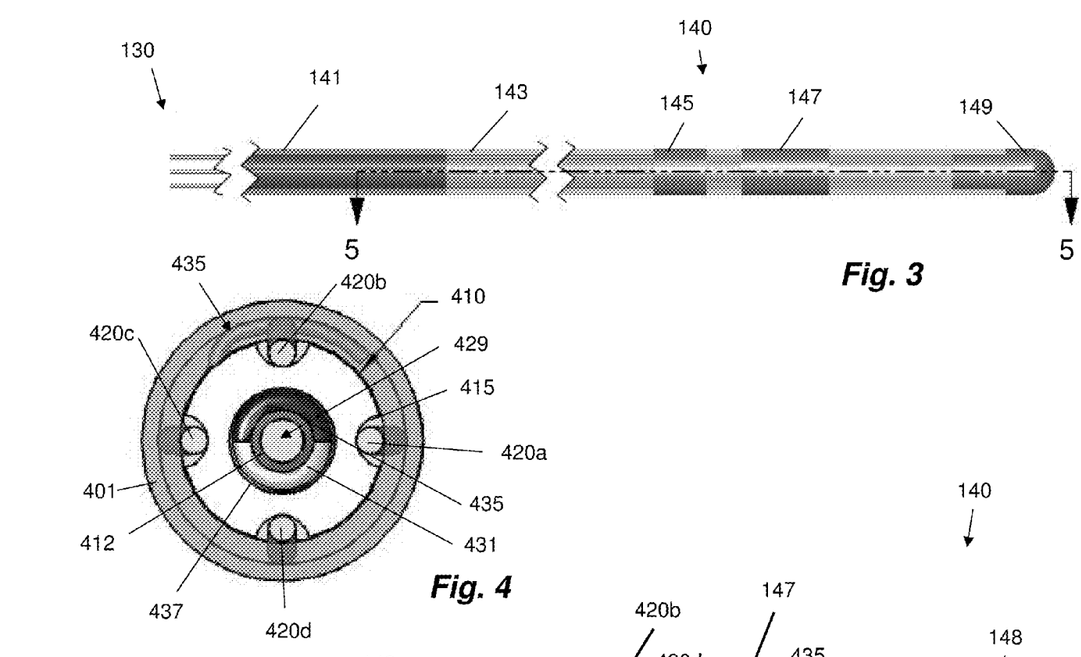
FIG. 3 is a side view of a distal end portion of an exemplary steerable catheter shaft assembly constructed in accordance with the invention.
FIG. 4 is a proximal end view of the steerable catheter shaft of FIG. 3.
Figure 5:
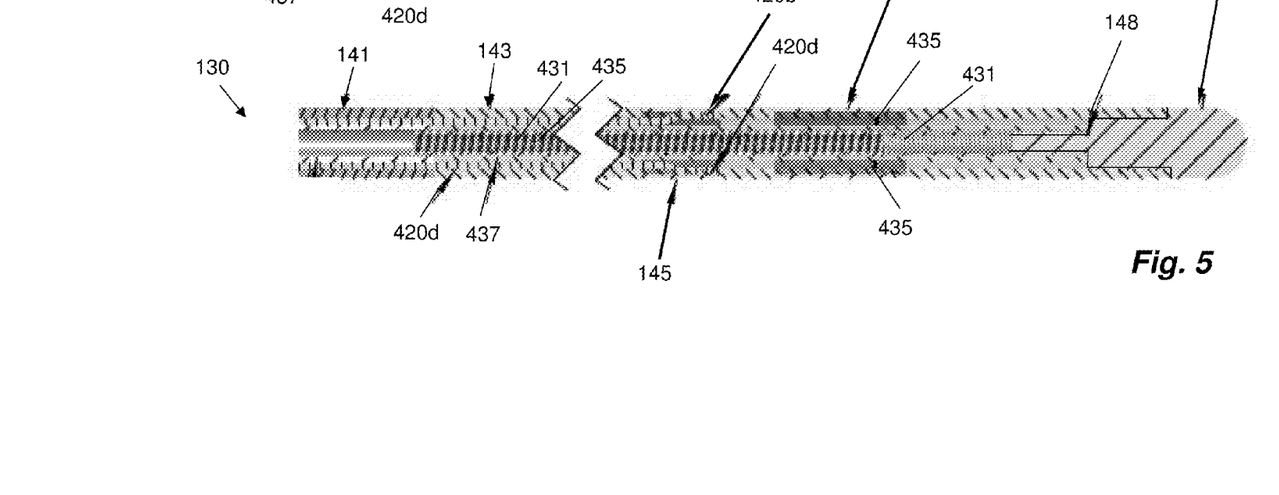
FIG. 5 is a longitudinal cross-sectional view of the steerable catheter shaft assembly of FIG. 3, taken across line 5-5 thereof.

Reference will now be made to FIGS. 3-5, which illustrate a side view, a proximal end view and a longitudinal cross-sectional view of a distal portion 140 of the shaft 130 of catheter lead assembly 100, respectively.

As illustrated, a proximal portion of the shaft 130, which includes a portion 141 of the shaft 130 proximal the distal portion 140 thereof, is preferably formed of a relatively stiff biocompatible material, including but not limited to a polyether block amide, such as PEBAX®, a fluoropolymer such as polytetrafluoroethylene (e.g. Teflon®), silicone or urethane, for example. The material selected preferably imparts sufficient rigidity to the shaft 130, such that insertion of the lead assembly 100 proceeds through the respective anatomical access path without buckling. However, the shaft 130 should be sufficiently flexible so as to allow the shaft 130 of the lead assembly 100 to bend sufficiently so to enable it to follow an anatomical pathway, through which the lead assembly 100 is inserted.

In accordance with one aspect, the structure of the shaft 130 includes among other features, outer stiff and flexible regions 141, 143 respectively. The material properties of the internal core 410 (e.g. FIG. 4) can be selected to correlate to those of the outer region of the shaft 130, with both flexible and stiff regions. Additionally or alternatively, the structure of selected sections can be configured to be more flexible, such as by providing a thinned or otherwise weakened material area, and/or segmentations with full or partial spaces therebetween, for example. Alternatively, the material of the core 410 can be continuous in material properties and/or physical configuration and/or the material on the outer portion of the shaft 130 can be continuous in material properties and/or physical configuration.

In accordance with an alternate aspect, the stiff and flexible properties can be predominantly the result of the material properties of the core 410 alone, with the outer surface of the shaft 130 being formed of a single material, such as silicone rubber or a urethane material, for example. Alternatively still, the stiff and flexible properties can be predominantly the result of the material properties of the outer surface of the shaft 130 alone, with the core 410 being formed of a single material, for example.

In the distal portion 140 of the shaft 130, at least one region 143 of a flexible, relatively soft and compliant material is provided, to allow the distal portion 140 to bend in response to control inputs, as will be described in more detail below. Optionally, and as illustrated, one or more electrodes 147, 149 can be incorporated into the distal portion 140 of the shaft 130. In accordance with one aspect, the proximal electrode 147 can be utilized as an anode, and the distal electrode 149 as a cathode. A fewer or greater number of electrodes can be provided, as required or desired. For example, one or more electrodes can be used for sensing, while one or more electrodes can be used for delivering a therapeutic electrical charge, such as for pulsing, ablation or another purpose.

As best seen in the cross-sectional views of FIGS. 4 and 5, although any number of conductors can be utilized, the illustrated embodiment includes two concentric helical conductors 431, 435, each respectively connected to one of the proximal electrode 147 and distal electrode 149. As illustrated, the helical conductors can optionally each have substantially the same diameter. In the illustrated embodiment, as shown in phantom line in FIG. 4, the first conductor 435 is lead out to the proximal electrode 147 and connected thereto in a suitable manner, such as by welding. The second conductor 431 continues distally to the distal electrode 149, and is connected thereto in a suitable manner, such as by a weld. Additionally, in the illustrated embodiment, the second conductor 431 is inserted over a reduced diameter proximal portion 148 of the distal electrode 149 to facilitate engagement therewith, while minimizing the diameter and enhancing the structural integrity of the shaft 130.

Within the shaft 130, as best seen in FIGS. 4 and 5, are arranged, concentric components including an outer body 401, an inner core 410, and a protective tube 437 applied between the core 410 and the conductors 431, 435. A further inner concentric tube 412 can be provided for protecting the conductors 431, 435 and/or for the purpose of insulating them from further inner concentric components and/or for providing further structural integrity. Moreover, an intervening insulative layer can be provided around, or alternatively between the conductors 431, 435, if provided. However, alternate insulation arrangements can be provided, such as those shown in U.S. Pat. No. 6,978,185 to Osypka and U.S. Pat. No. 7,158,837 to Osypka et al., which patents are incorporated herein by reference in their entirety.

As best seen in FIG. 4, a plurality of circumferentially spaced steering wires 420a, 420b, 420c, 420d are provided in channels formed in the core 410. The steering wires 420a, 420b, 420c, 420d are connected at their distal end to a steering ring 145 in the distal end portion 140 of the shaft 130. The connection therebetween can be made by any suitable means, including but not limited to welding thereto.

As best seen in FIG. 6, the steering wires 420a, 420b, 420c, 420d are connected to the control assembly 200. As mentioned above, the control assembly 200 includes a swivel joint 280, which in the illustrated embodiment is a spherical ball joint. The swivel joint 280 allows for multi-axis movement of the control handle 120, which is mounted thereon by way of a socket portion 685 thereof. As illustrated, the control handle 120 and socket 685 are also connected to one or more flanges 681, 683, which engage the steering wires 420a, 420b, 420c, 420d, and function as a control yoke for manipulating the steering wires 420.

In the illustrated embodiment, the steering wires 420a, 420b, 420c, 420d include terminations 621. The steering wires 420a, 420b, 420c, 420d are inserted into radial grooves 684 formed in the proximal flange 683, and the terminations 621 inhibit the steering wires 420a, 420b, 420c, 420d from pulling through their designated groove. As shown, the proximal flange 683 is integrally formed with the socket 685, and is mechanically connected to the distal flange 681, by a plurality of bolts 687. Alternative connections can be substituted as desired or required. If desired, the socket 685 can be maintained in position on the ball of the swivel joint 280 by distally directed tension. As illustrated, the distal flange 681 is brought into connection with the proximal flange 683 after the ball 281 is accepted within the socket 685. The distal flange 681 can be inserted on the stem 250 from the distal end thereof, or alternatively, can be provided in two or more split parts, and separately connected to the proximal flange 683 to secure the control handle 120, socket 685 and the proximal and distal flanges 683, 681 to the ball 284 of the swivel joint 280. In such instance, an inner diameter of the distal flange 681 is selected to be between an outer diameter of the stem 250 and an outer diameter of the ball 284 of swivel joint 280, to maintain secure connection therebetween and to inhibit removal therefrom.

As illustrated, the steering wires 420a, 420b, 420c, 420d are provided, and spaced circumferentially respectively separated by about 90 degrees. Accordingly, wire 420b is referred to herein as the "top" steering wire, wire 420d as the "bottom" steering wire, wire 420a as the "right" steering wire and wire 420c as the "left" steering wire. The top and bottom steering wires 420b, 420d extend through respective slots 686 formed in the distal flange 681 and are held therein by the respective steering wire terminations 621. The control handle 120 is illustrated in FIG. 6 in a right position, but when in a neutral position, the top slot 686 aligns with a neutral position of the top steering wire 420b, while the bottom steering wire 420d is accepted in a similar arrangement in an opposed slot.

The left and right steering wires 420c, 420a are engaged by the respective slots 684, and extend through slots 682, which are, as illustrated, preferably rounded or include other adaptations to minimize kinking and/or chafing of the left and right steering wires 420c, 420a extending therethrough. The left and right steering wires 420c, 420a, as illustrated, extend over laterally (also radially) extending pins 615. Rotational movement of the control handle 120 toward the left or right side, with respect to the body, results in increased tension applied to the steering wire 420c, 420a on the same side. As such movement (e.g. to the right, as illustrated) is applied, the opposite steering wire 420a, 420c (e.g. left steering wire 420c) rises above its respective pin 615, from a neutral position. Although some tension may be applied to that opposite steering wire (e.g. left steering wire 420c), the tension applied to the wire corresponding to the intended direction (e.g. right steering wire 420a) is greater and compensates for any tension applied to the opposite steering wire (e.g. left steering wire 420c). Accordingly, the tension applied to the steering wires 420a-d extends through the shaft 130 to the steering ring 145, which responds by moving in the respective direction, and along with it, the distal end portion 140 of the shaft 130. In the embodiment illustrated, most bending occurs in the flexible material region 143 between the stiff material region 141 and the steering ring 145 (e.g. FIG. 3), however variations of this arrangement are conceived.

Upward and downward movement of the distal end portion 140 is effected by selectively tensioning the respective steering wire 420c, 420d. As embodied, the control handle 120 is moved backward (proximally) or forward (distally), pivoting on the swivel joint 280, to achieve the desired response of the shaft 140. Combined directional movements can be effected by tensioning multiple adjacent steering wires. For example, top and right steering wires 420b, 420d can be tensioned to effect upward and rightward directed movement of the distal end 140 of the shaft 130 by moving the control handle 120 to the right and backward (proximally).

The pins 615 can be provided at about the center line of the stem 250, or alternatively can be offset therefrom. As set forth above, the displacement caused by the pins 615 causes increased tension in respective steering wires, as compared with the opposite steering wires. Alternatively, the pins can be offset from the central axis by set distance, such that in a neutral position, the left and right steering wires 420a, 420c are deflected by the pins 615. In such an arrangement, tension is applied to the desired steering wire as it is forced to deflect further, and tension in the opposite steering wire is relaxed, as it is allowed to straighten. In such an arrangement, the pins 615 on both sides of the stem 250 in the embodiment of FIG. 6 are arranged somewhat above the central axis of the stem 250, such that each steering wire is deflected by running across an upper surface of the respective pin 615, as is illustrated.

As shown in the end view FIG. 4, inserts 415 can be provided in the core 410, corresponding with each steering wire 420. The inserts can serve to protect the core material and/or the steering wires 420 from abrasion due to relative movement therebetween. The inserts 415 can be provided along the length of the catheter, or alternatively can be provided only at the proximal end thereof such that movement due to manipulation of the steering wires 420 does not adversely affect the integrity of the material of the core 410.

The core 410 of the shaft 130, can be provided with a central lumen 429, which remains open. The lumen 429 can be adapted to hold an internal rigidifying member, such as an obturator or the like, to facilitate insertion of the catheter 100 through a patient's vein or other anatomical pathway. Alternatively, the lumen 429 can be adapted to deliver medicaments to a surgical site, through one or more apertures that can be defined through the wall of the distal end portion 140 of the catheter shaft 130. Alternatively still, the shaft 130 can be provided without a hollow lumen.

As set forth above, any suitable biocompatible materials can be used for the construction of devices in accordance with the invention. The material of the core 410, in accordance with one aspect, is selected from one or more of polyether block amide, such as PEBAX®, a fluoropolymer such as polytetrafluoroethylene (e.g. Teflon®), silicone or urethane. The materials used for the outer surface components of the shaft 130 can also be selected from this group of materials. The electrodes 147,149 can be made of any suitable biocompatible electrically conductive material, such as a metal alloy, for example a stainless steel. The steering wires 420 can be formed of a suitable polymeric or metal material, which is preferably compatible with the material used to form the steering ring 145 to facilitate attachment thereto. The material selected for the steering wires 420 and the steering ring 145 in accordance with one aspect of the invention is a weldable metal material, such as a stainless steel alloy or a shape memory alloy, such as a nickel-titanium alloy (e.g. Nitinol), for example.

The electrical conductors 431, 435 can be any suitable material including but not limited to stranded stainless steel, copper, drawn filled tube (DFT) formed of any suitable materials or other conductors, and each conductor can be independently insulated, if desired.

Figure 7:
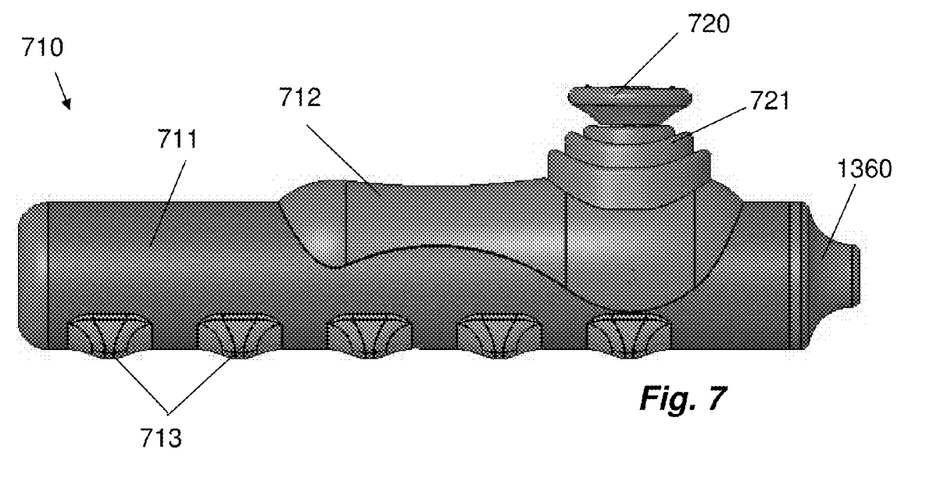
FIG. 7 is a side view of a handle of a further embodiment of a catheter control mechanism constructed in accordance with the present invention.

A further catheter control mechanism constructed in accordance with the invention is shown in FIG. 7, and designated by reference number 710.

Figure 8:
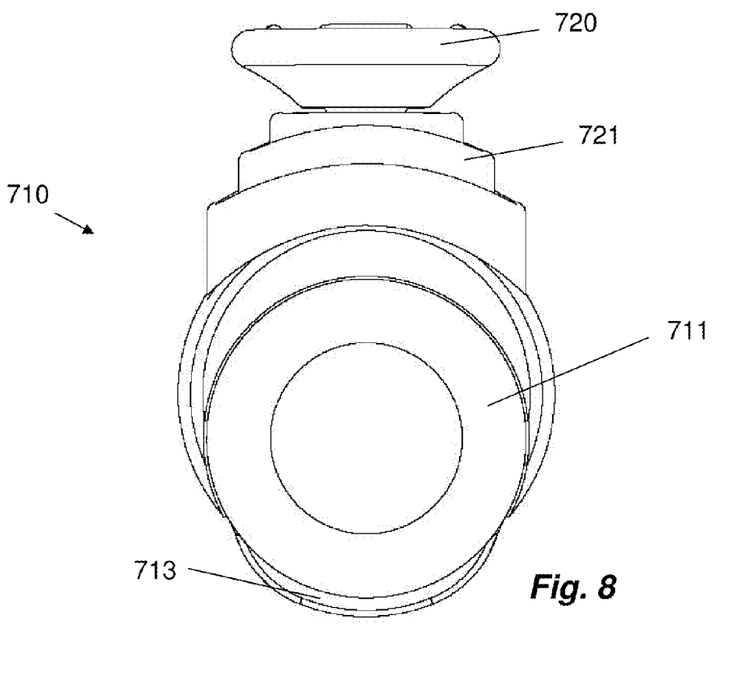
FIG. 8 is a rear end view of the handle illustrated in FIG. 7.

The catheter control mechanism 710, as seen in the external views of FIGS. 7 and 8, includes a handle 711, a control lever 720, a gaiter 721 for sealing between the handle 711 and the control lever 720, an upper grip 712 and lower grip 713 to facilitate secure handling by a user, such as a physician.

Figure 9:
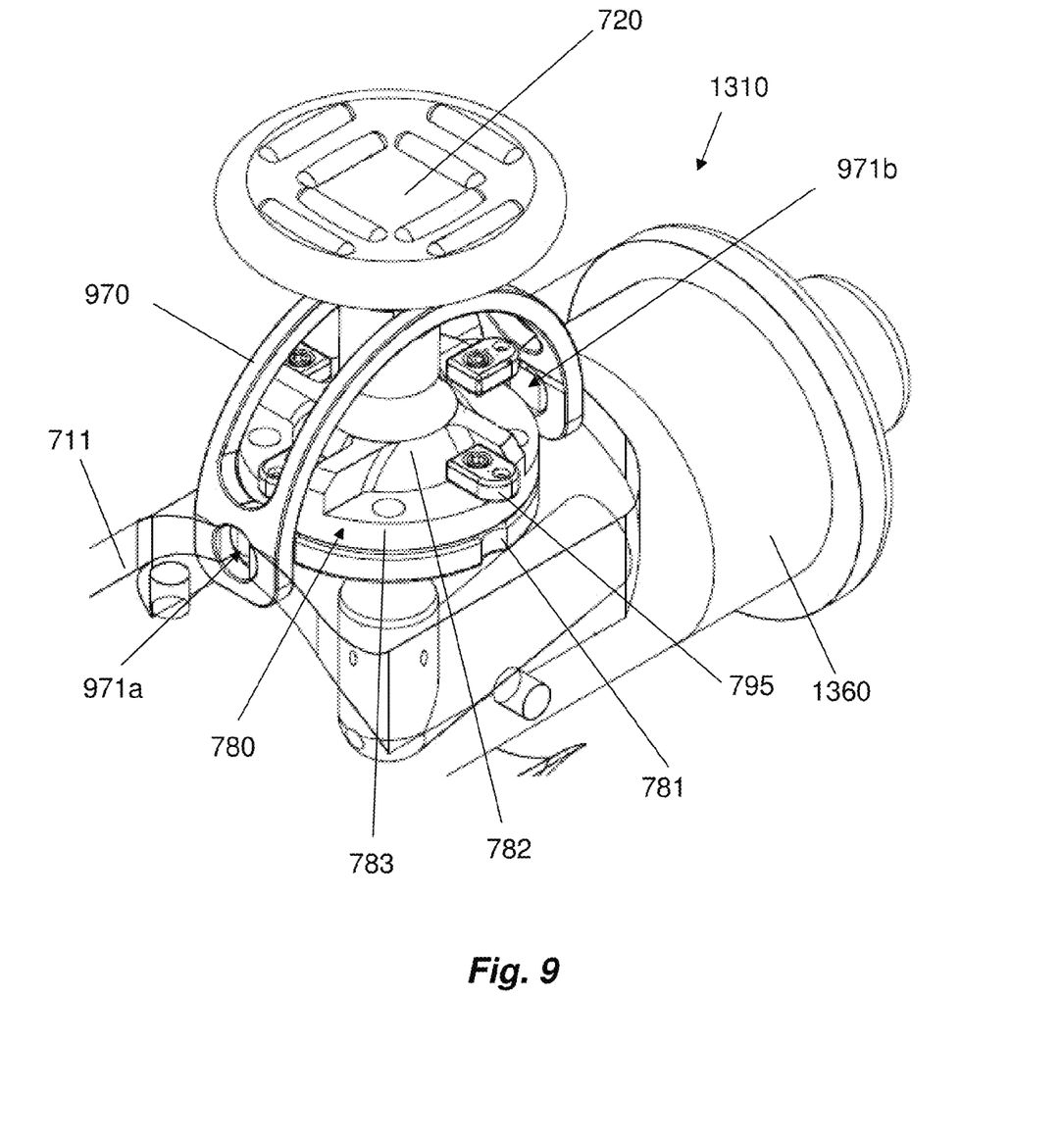
FIG. 9 is an isometric partial cutaway view, illustrating internal components of the catheter control mechanism provided in connection with the handle illustrated in FIG. 7.
Figure 10:
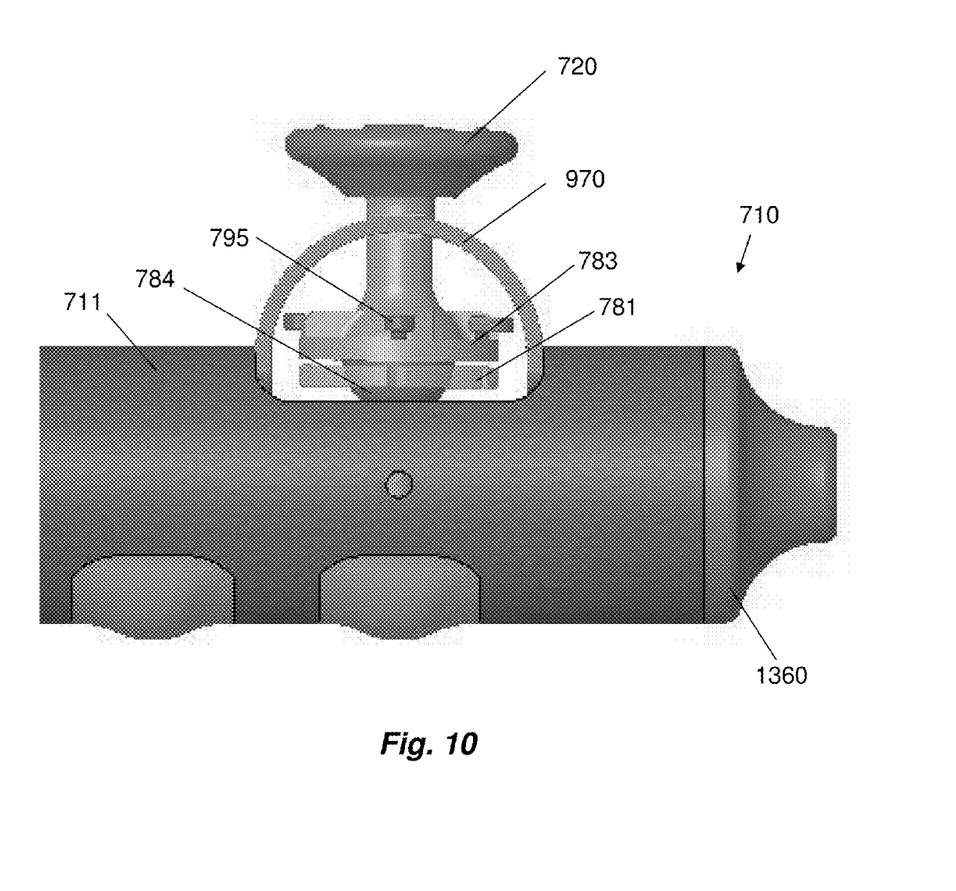
FIG. 10 is a side partial cutaway view, illustrating of the catheter control mechanism of FIG. 9.
Figure 11:
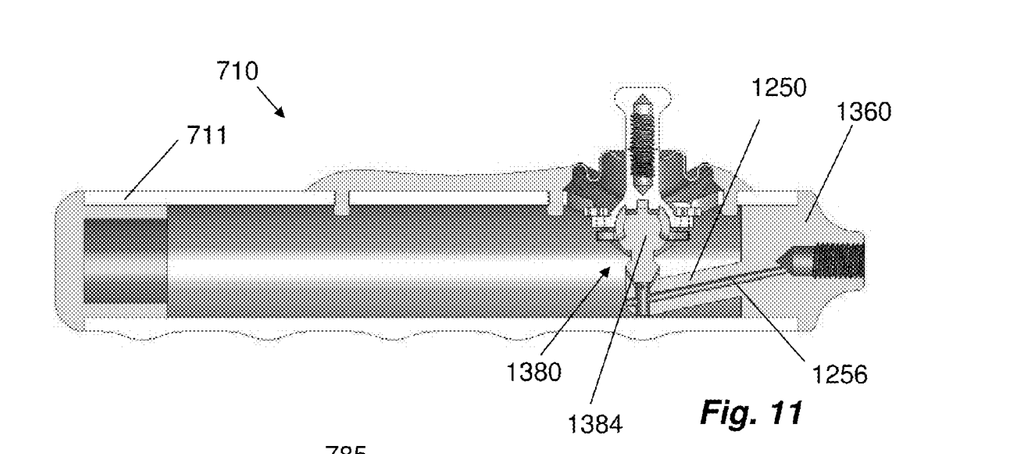
FIG. 11 is a longitudinal cross-sectional view illustrating internal components of the catheter control mechanism of FIG. 9.

As best seen in the internal views of FIGS. 9 and 10, the control lever 720 is connected to a swivel joint 780, including a yoke 782, on which a plurality of catheter steering wire-engaging elements 795 are orthogonally arranged. The lever 720 is supported from below by the yoke 782, and is optionally supported in the upper portion by a stabilizer 970. The stabilizer 970 is pivotably connected to the handle 711 at its lower ends, as indicated by reference numbers 971a and 971b.

As seen in FIGS. 10-16, for example, the swivel joint 780 also includes a ball portion 784 that supports the yoke 782, and which in-turn is supported by a stem 1250, extending from a proximal end cap 1360, secured to the handle 711. The yoke 782 is secured to the ball portion 784 by way of an integral upper flange 783 and separate lower flange portions 781, which are secured thereto from below and which, in conjunction with the yoke 782, securely captures the ball portion 784.

Figure 12:
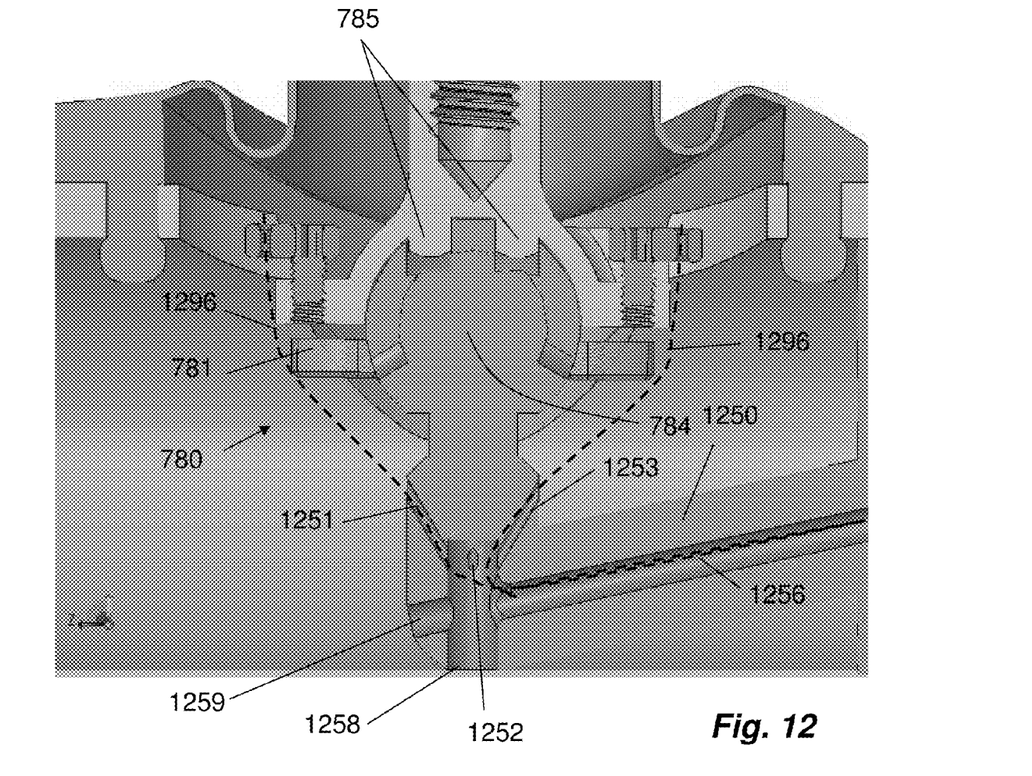
FIG. 12 is a detail cross-sectional view illustrating internal components of the catheter control mechanism of FIG. 9.
Figure 13:
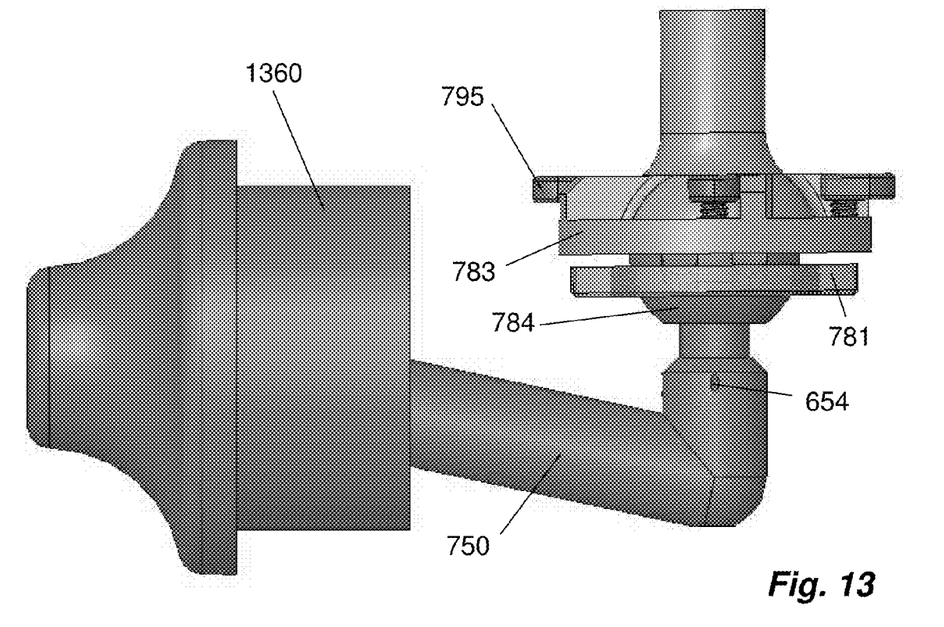
FIG. 13 is a side view illustrating the internal components of the catheter control mechanism of FIG. 9.
Figure 14:
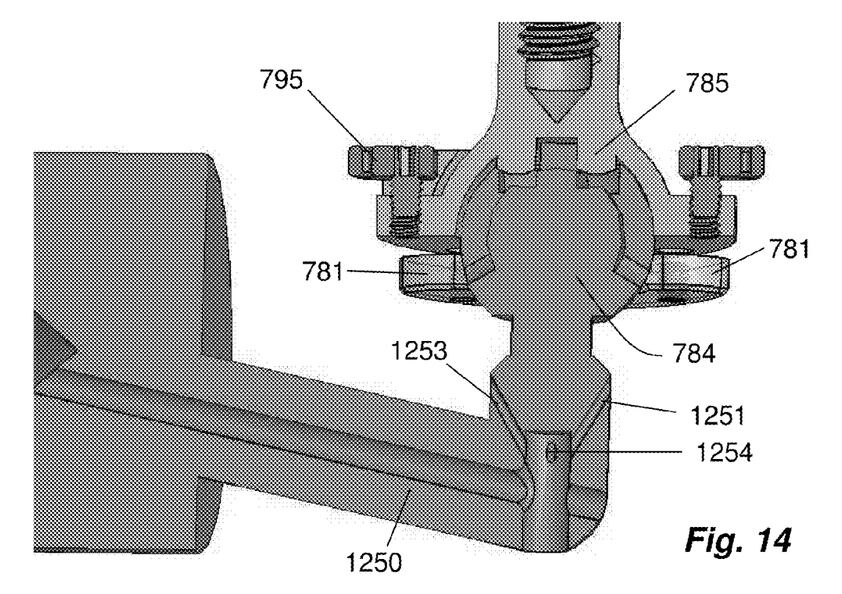
FIG. 14 is a side cross-sectional view illustrating the internal components of the catheter control mechanism of FIG. 9.
Figure 15:
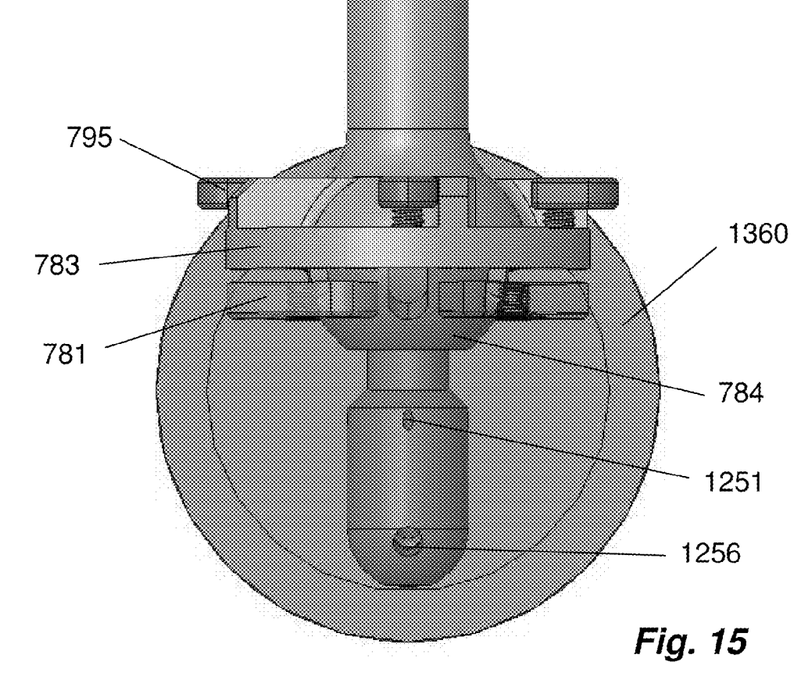
FIG. 15 is a rear view of the internal components of the catheter control mechanism of FIG. 9.
Figure 16:
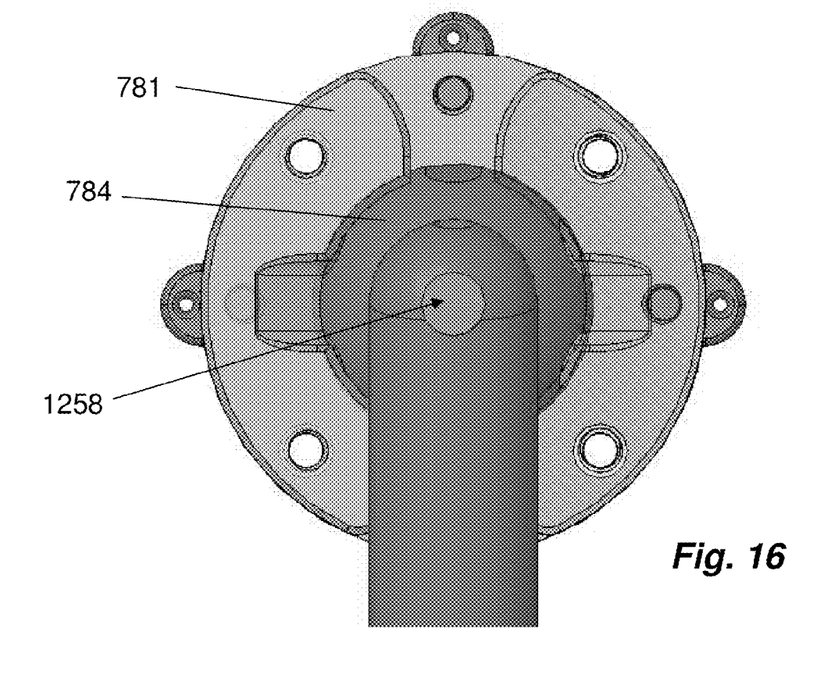
FIG. 16 is a bottom view of the internal components of the catheter control mechanism of FIG. 9.
Figure 17:
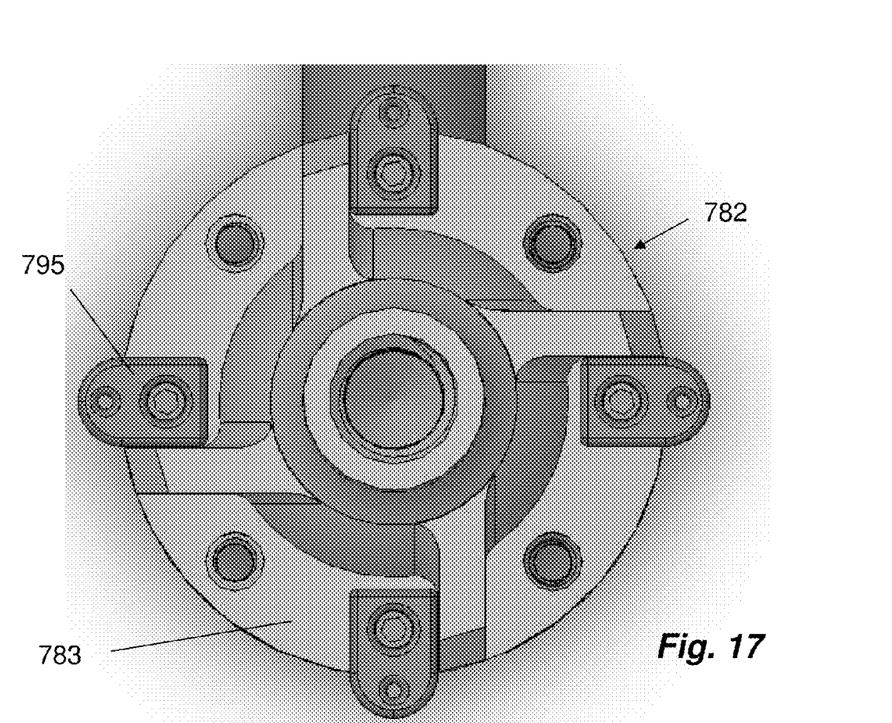
FIG. 17 is a top view of the internal components of the catheter control mechanism of FIG. 9.
Figure 18:
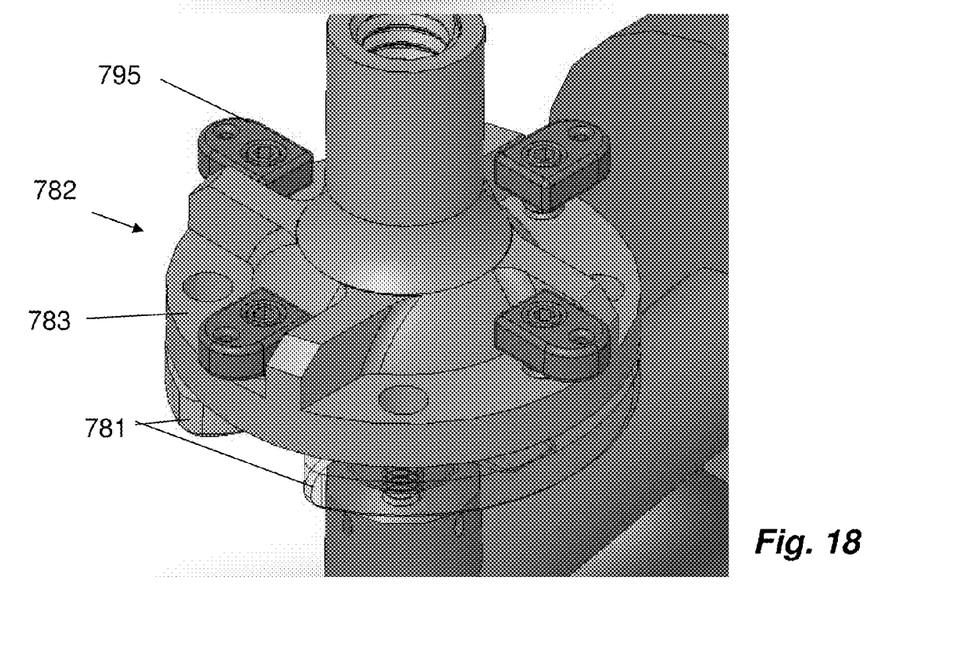
FIG. 18 is a top isometric view of the internal components of the catheter control mechanism of FIG. 9.
Figure 23:
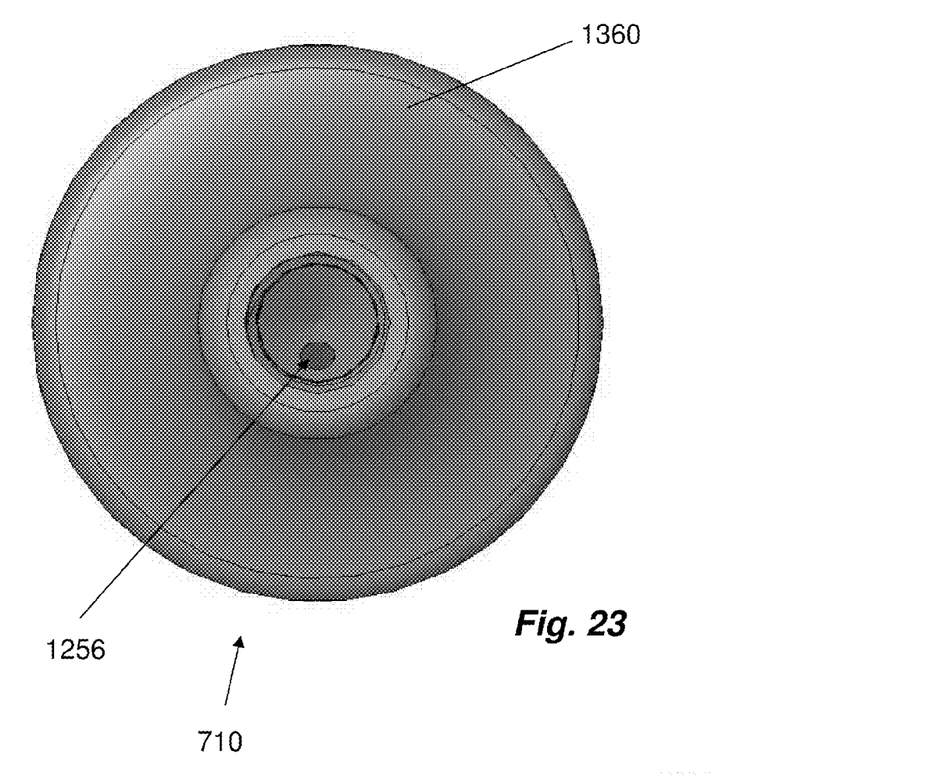
FIG. 23 is a front end view of the catheter control mechanism of FIG. 7.

Catheter steering wires 1296, represented by dashed lines in FIG. 12, are connected to the steering wire engaging elements 795 at one end, and are routed downward into corresponding orthogonally arranged apertures 1251, 1252, 1253, 1254 formed in the stem 1250, through a passage 1256 connected therethrough and through the front end cap 1360 of the control mechanism 710, where the control mechanism 710 engages a catheter (see FIG. 23).

The passage 1256 formed in the stem 1250 is optionally provided with a lower access opening 1258 and an end access opening 1259 to facilitate threading of the catheter steering wires 1296 through the stem 1250 and to the steering wire engaging elements 795.

Figure 19:
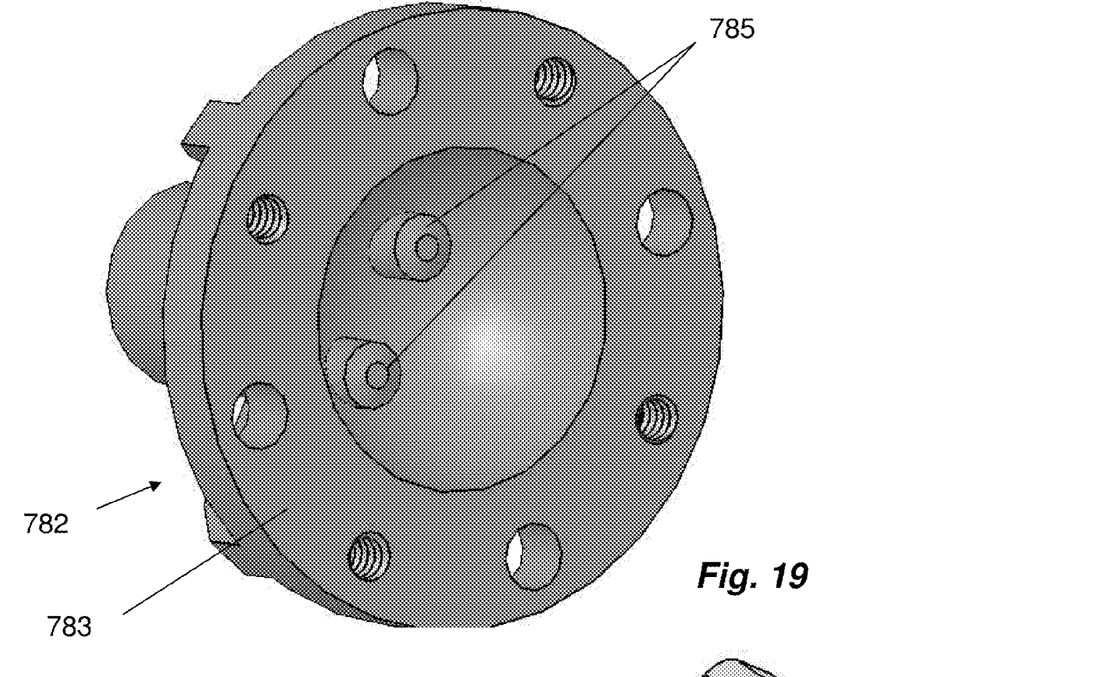
FIG. 19 is a bottom isometric view of a yoke portion of the catheter control mechanism of FIG. 9.
Figure 20:
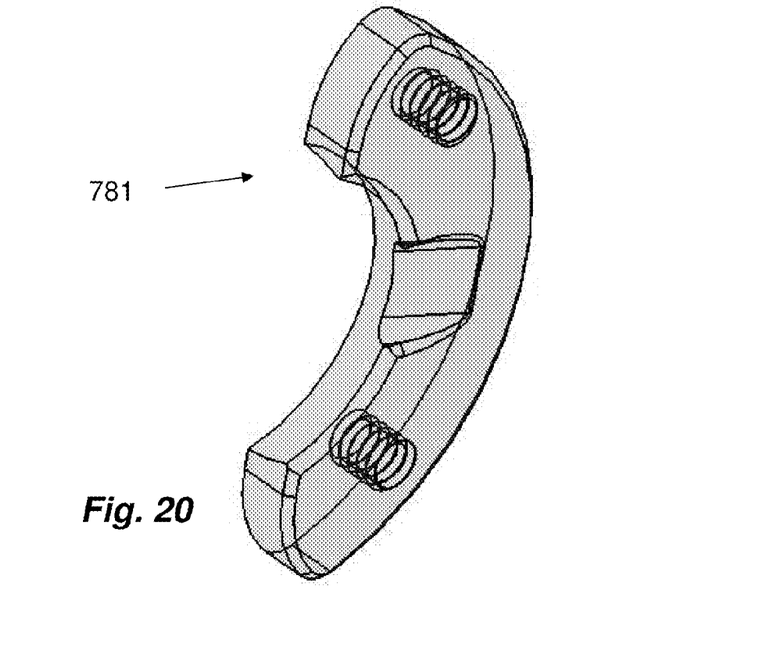
FIG. 20 is a bottom isometric view of a bottom flange portion for engaging the yoke of FIG. 19 with a swivel joint.
Figure 21:
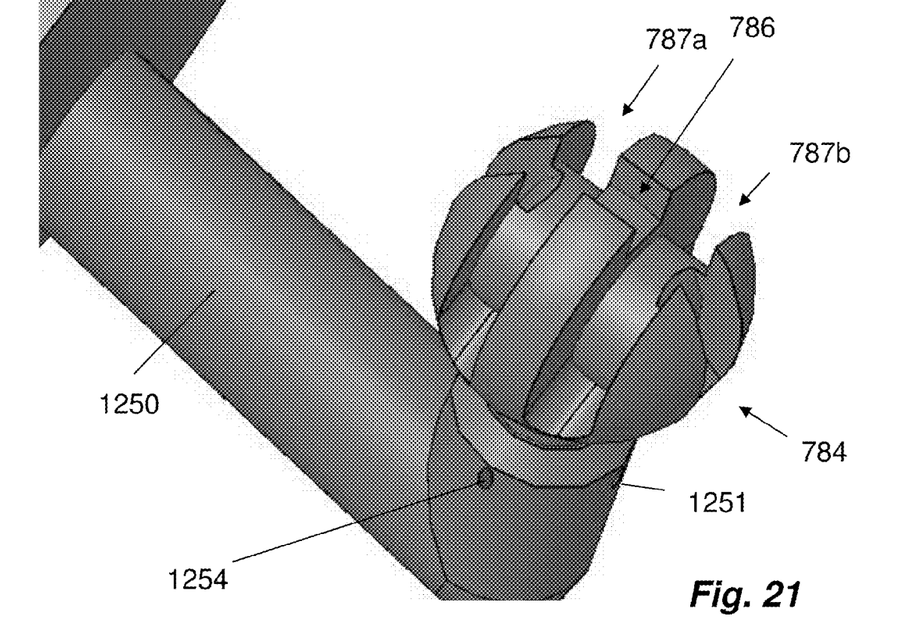
FIG. 21 is a top side isometric view illustrating the configuration of a ball portion of the swivel joint of the catheter control mechanism of FIG. 9.
Figure 22:
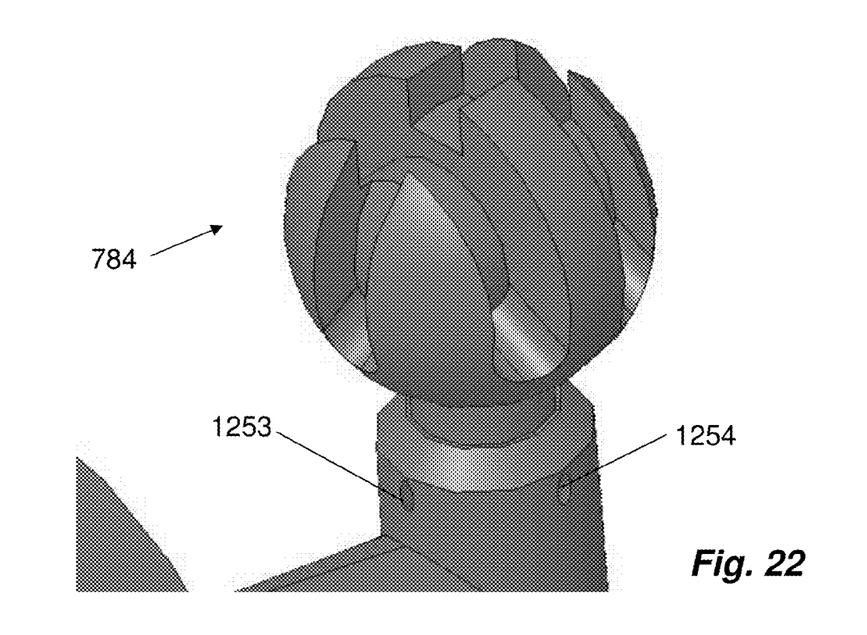
FIG. 22 is a front top isometric view illustrating the configuration of the ball portion of the swivel joint of the catheter control mechanism of FIG. 9.

For the purpose of providing a further, non-limiting example of a control mechanism in accordance with the invention, and as best seen in FIGS. 12, 14, 19, 21 and 22, the swivel joint 780, and particularly the ball portion 784 and the control yoke 782, are configured for mutually exclusive orthogonal movement, the handle 711 being restrained to either forward-backward movement or left-right movement at any one moment. With reference to FIGS. 19, 21 and 22, the yoke 782 includes, on its bottom surface, yoke guides 785 extending therefrom. The guides 785 are provided in a colinear arrangement corresponding to a longitudinal channel 786 formed in the ball portion 784. Accordingly, forward and backward movement of the yoke 782, in line with the guides 785 and the channel 786, is permitted. Additionally, the guides 785 individually align with lateral channels 787a, 787b formed in the ball portion 784, permitting side-to-side movement of the yoke 782 with respect to the ball portion 784. The configuration of the channels 786, 787a, 787b formed in the ball portion 784, as illustrated, permits only exclusive side-to-side (lateral/circumferential) or forward-backward (longitudinal) movement of the yoke 782 and handle 720 at any moment. Such an arrangement advantageously guides the user more precisely in each respective motion.

Alternatively, if desired, such lateral and longitudinal restrictions can be omitted by eliminating the guides 785 and/or the channels 786, 787a, 787b. Alternatively still, constraints on movement can be altered by modifying the arrangement of guides and/or channels accordingly. Moreover, such features can advantageously be applied to the embodiment of FIGS. 1-6, for example.

In the illustrated embodiment, the side-to-side (lateral/circumferential) movement of the control lever 720 causes the yoke 782 to pull upward on the respective one of the side steering wire engaging elements 795, to which catheter steering wires 1296 are attached, and forward-backward (longitudinal) movement of the control lever 720 causes the yoke 782 to pull upward on the respective one of the front or back steering wire engaging elements 795. Accordingly, tension is applied to one of the steering wires 1296 which is carried through the attached catheter, effecting bending thereof, typically at the distal end portion of the catheter, as described above, but depending on the configuration thereof. The catheter steering wires 1296 can be configured and connected to the yoke 782 such that left-directed motion of the lever 720 applies tension to a left steering wire 1296, effecting left bending of the catheter, and so-on for each of the orthogonal directions.

Figure 24:
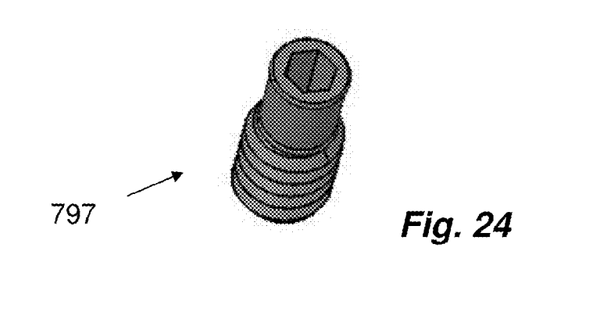
FIG. 24 is an isometric view of a screw for connecting a catheter steering wire-engaging element to a yoke portion of the catheter control mechanism of FIG. 9.
Figure 25:
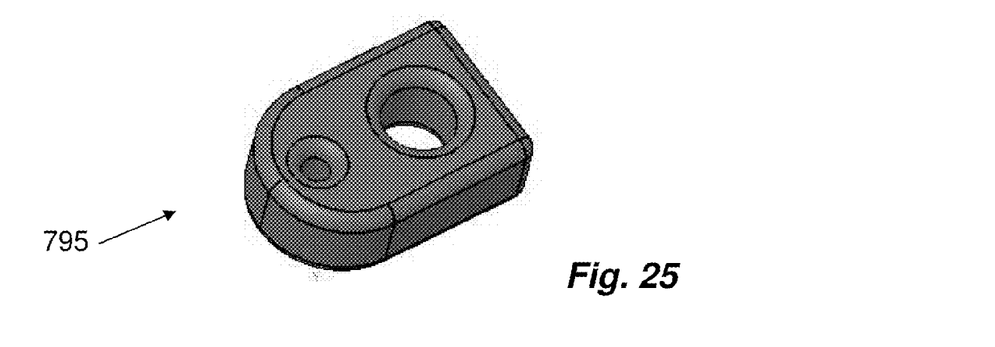
FIG. 25 is an isometric view of a steering wire-engaging element of the catheter control mechanism of FIG. 9.

If desired, tension applied to the steering wires 1296 can be adjusted by adjusting the relative spacing between the upper flange 783 and the steering wire engaging elements 795, by adjusting the screw 797 therebetween, a detail view of which is shown in FIG. 24.

The devices and related methods of the present invention, as described above and shown in the drawings, provide for catheter control mechanisms and catheter constructions that are durable and permit intuitive control thereof. It will be apparent to those skilled in the art that various modifications and variations can be made to the devices and related methods of the present invention without departing from the spirit or scope of the invention. Thus, it is intended that the present invention include modifications and variations that are within the scope of the appended claims and their equivalents.

What is claimed is:

1. A control assembly for a steerable catheter comprising:
   a) a handle including a generally cylindrical housing having a longitudinal axis extending therethrough;
   b) a swivel joint including a generally spherical ball portion supported within the housing of the handle by a stem, wherein the swivel joint is configured to facilitate side-to-side angular movement of the control yoke about a first axis extending parallel to the longitudinal axis of the handle and forward-to-backward angular movement of the control yoke about a second axis that extends perpendicular to the first axis;
   c) a control yoke having a generally annular flange surrounding the ball portion of the swivel joint and supported for angular movement relative thereto;
   d) a plurality of circumferentially spaced apart steering wire engagement elements mounted on the flange of the control yoke, each for retaining a corresponding catheter steering wire; and
   e) a control lever connected to the control yoke for controlling the angular movement thereof and corresponding movement of a plurality of catheter steering wires connected to the steering wire engagements elements, wherein the stem includes an interior passage for routing the plurality of catheter steering wires from the annular flange of the control yoke through the housing of the handle to a catheter shaft extending distally from the handle.

2. A control assembly as recited in claim 1, wherein the control lever is supported within a semi-circular stabilizer that has a track to guide the forward-to-backward angular movement of the control yoke.

3. A control assembly as recited in claim 2, wherein each end of the semi-circular stabilizer is pivotally connected to the handle to guide the side-to-side angular movement of the control yoke.

4. A control assembly as recited in claim 1, wherein a pair of collinear yoke guides extend from an undersurface of the control yoke for interacting with corresponding guide channels formed in the ball portion of the swivel joint to guide the forward-to-backward angular movement of the control yoke.

5. A control assembly as recited in claim 1, wherein a pair of collinear yoke guides extend from an undersurface of the control yoke for interacting with corresponding guide channels formed in the ball portion of the swivel joint to guide the side-to-side angular movement of the control yoke.

6. A control assembly as recited in claim 1, wherein a catheter shaft extending distally from the handle includes a flexible distal portion which is manipulated by the plurality of steering wires extending from the control yoke.

7. A control assembly as recited in claim 6, wherein a plurality of axially spaced apart electrodes are operatively positioned on the flexible distal portion of the catheter shaft.

* * * * *